(12) United States Patent
Noda et al.

(10) Patent No.: US 7,641,618 B2
(45) Date of Patent: Jan. 5, 2010

(54) CAPACITANCE-TYPE PRESSURE SENSOR AND HEART BEAT / RESPIRATION MEASURING DEVICE USING THE SAME

(75) Inventors: Satoshi Noda, Hirakata (JP); Takeshi Minamiura, Osaka (JP); Hidetaka Sakai, Katano (JP); Fumiiki Yoneda, Moriguchi (JP)

(73) Assignee: Sanyo Electric Co., Ltd., Osaka (JP)

( * ) Notice: Subject to any disclaimer, the term of this patent is extended or adjusted under 35 U.S.C. 154(b) by 648 days.

(21) Appl. No.: 11/082,890

(22) Filed: Mar. 18, 2005

(65) Prior Publication Data

US 2005/0215915 A1    Sep. 29, 2005

(30) Foreign Application Priority Data

Mar. 29, 2004 (JP) ............................. 2004-094880
Sep. 21, 2004 (JP) ............................. 2004-273903

(51) Int. Cl.
  *A61B 5/08* (2006.01)
(52) U.S. Cl. ...................... 600/535; 600/529
(58) Field of Classification Search ......... 600/529–543; 428/209; 324/318, 322, 658–690; 361/283.1–283.4
  See application file for complete search history.

(56) References Cited

U.S. PATENT DOCUMENTS 6,809,462 B2 * 10/2004 Pelrine et al. ............... 310/319

FOREIGN PATENT DOCUMENTS

| JP | 5-200001 | 8/1993 |
| JP | 9-269379 | 10/1997 |
| JP | 2002-90213 | 3/2002 |
| JP | 2003-339652 | 12/2003 |
| JP | 2004-020440 | 1/2004 |
| WO | WO 9822836 A1 * | 5/1998 |

OTHER PUBLICATIONS

AIPO Japan Patent Office—machine translation of JP 2003339652 A.*
Japanese Office Action issued in Japanese Patent Application No. 2004-273903 dated on Oct. 30, 2007.
Japanese Final Office Action issued in Japanese Patent Application No. 2004-273903 dated on Feb. 12, 2008.

(Continued)

*Primary Examiner*—Charles A Marmor, II
*Assistant Examiner*—Christian Y Jang
(74) *Attorney, Agent, or Firm*—McDermott Will & Emery LLP

(57) ABSTRACT

A heart beat/respiration measuring device comprising a sheet-like capacitance-type pressure sensor adapted to be pressed against the human body, and a measuring circuit for measuring a heart rate and/or respiration rate from the output of the sensor. The capacitance-type pressure sensor includes a sheet-like dielectric body elastically deformable in all directions and a pair of conductive clothes with stretchability disposed on opposite sides of the dielectric body. The measuring circuit comprises a resonant circuit wherein the capacitance-type pressure sensor serves as an oscillation capacitor, and a calculation processing circuit for detecting variations in the oscillation frequency of the resonant circuit and calculating the heart rate and/or respiration rate based on the frequency component or components of heart beats and/or respiration included in the variations.

11 Claims, 16 Drawing Sheets

OTHER PUBLICATIONS

Ishiijima "Cardiopulmonary Monitoring by Textile Electrodes without Subject-Awareness of Being Monitored" Institute of Biomedical Engineering, Tokyo Women's Medical College, Tokyo, Japan, pp. 685-690 Nov. 1997.

Masayuki "Health Monitoring System for Elderly People Staying at Home 1998 (study related to cardiopulmonary monitoring for the purpose of long term observation)" Health, Labor, and Welfare Ministry, Grants for Health Science (Comprehensive Research Project for Longevity Science) Cooperative Research Report 19999, pp. 7-10.

* cited by examiner

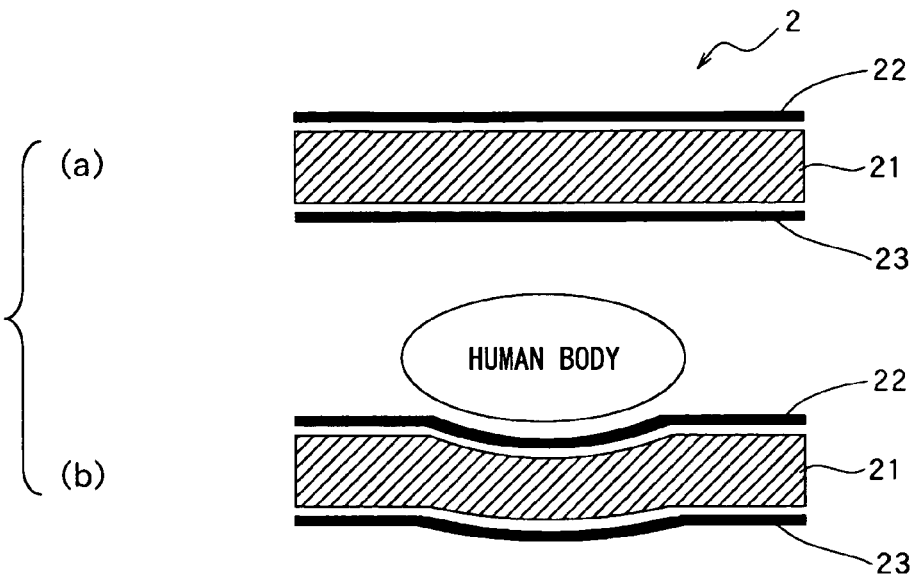
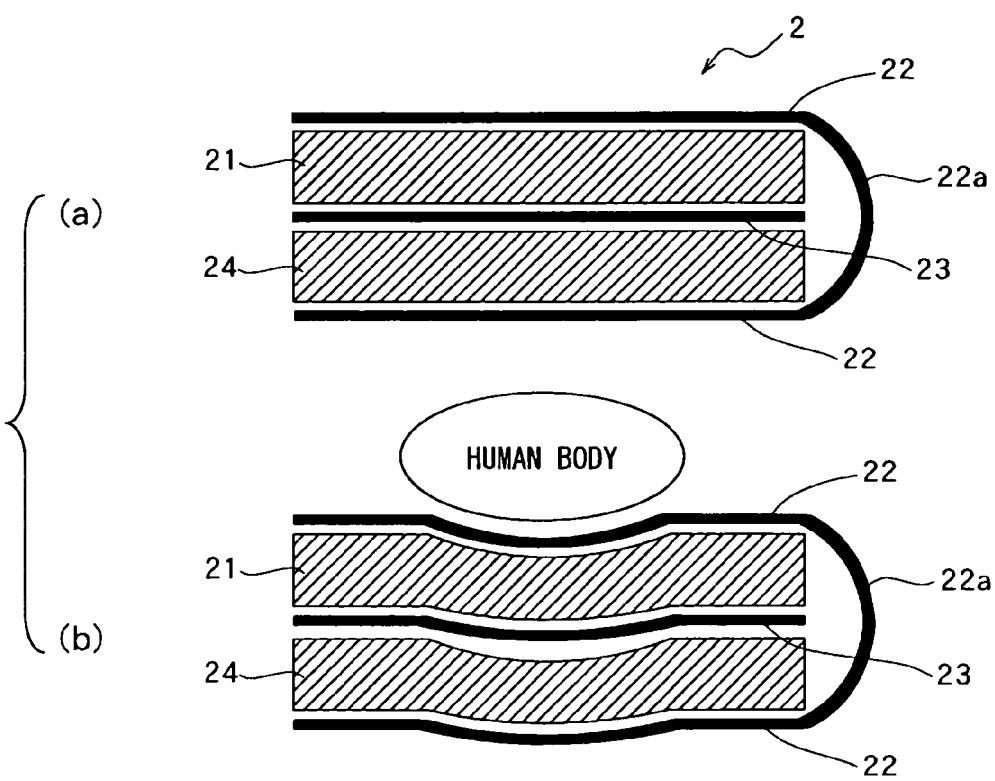

CAPACITANCE-TYPE PRESSURE SENSOR AND HEART BEAT / RESPIRATION MEASURING DEVICE USING THE SAME

BACKGROUND OF THE INVENTION

1. Field of the Invention

The present invention relates to a capacitance-type pressure sensor and heart beat/respiration measuring device using the same.

2. Description of the Related Art

With the aging of society in recent years, there is an increase in the number of bedridden elderly persons, and attention has been directed to the method of conducting diagnosis based on variations in the heart rate as measured by an electrocardiograph as a method of monitoring the physical condition of the bedridden elderly persons (see JP-A No. 200001/1993 and 269379/1997). Presently, with growing awareness of health management, people have become more desirous of readily measuring the heart rate during sleep in the ordinary family.

However, when the conventional electrocardiograph is to be used for measuring the heart rate, there is a need to affix a plurality of conductive members directly to the skin, and the conventional device therefore has the drawback that the person to be checked is held restrained for a prolonged period of time by the cords extending from the conductive members to the main body of the instrument. Because of the same situation involved in measuring the respiration rate, difficulty is encountered in making the measurement easily in the home.

Accordingly, the applicants have proposed a capacitance-type pressure sensor including a pair of sheet-like conductive members made of copper foil and a dielectric body made of urethane inserted therebetween, and a heart beat/respiration measuring device using the sensor (see JP-A No. 339652/2003). The heart beat/respiration measuring device can measure a heart rate or respiration rate of a human body free of restraint, so that diagnosis in a sleeping state can be easily conducted in the home. However, the above-described heart beat/respiration measuring device proposed by the applicants still remains to be improved with respect to the measurement accuracy and sensitivity.

SUMMARY OF THE INVENTION

An object of the present invention is to provide a capacitance-type pressure sensor and a heart beat/respiration measuring device which are adapted to measure the heart rate or respiration rate of the human body free of restraint and with high accuracy and sensitivity.

The present invention provides a heart beat/respiration measuring device comprising a sheet-like capacitance-type pressure sensor 2 adapted to be pressed against a human body, and a measuring circuit for measuring a heart rate and/or respiration rate from the output of the sensor 2. The measuring circuit comprises a resonant circuit 3 wherein the capacitance-type pressure sensor 2 serves as an oscillation capacitor, and a calculation processing circuit 4 for detecting variations in the oscillation frequency of the resonant circuit 3 and calculating the heart rate and/or respiration rate based on the frequency component or components of heart beats and/or respiration included in the variations.

The capacitance-type pressure sensor 2 comprises a sheet-like dielectric body 21 elastically deformable in all directions and a pair of conductive clothes with stretchability 22, 23 disposed on opposite sides of the dielectric body. Alternatively, two sheet-like dielectric bodies 21, 24 elastically deformable in all directions are superposed on each other with one conductive cloth 23 interposed therebetween, and two conductive clothes 22, 22 are disposed on opposite sides of the two sheet-like dielectric bodies 21, 24 with the two conductive clothes 22, 22 electrically connected to each other. The resonant circuit 3 may be an LC oscillation circuit or a CR oscillation circuit wherein the capacitance-type pressure sensor 2 serves as an oscillation capacitor.

With the heart beat/respiration measuring device of the present invention, the capacitance-type pressure sensor 2 is installed under the human body lying in a dorsal position, prone position or lateral position. Accordingly, the capacitance-type pressure sensor 2 is subjected to pressure fluctuation by being pressed with the heart beats and respiration of the human body. Consequently, the sheet-like dielectric body 21 of the capacitance-type pressure sensor 2 is elastically deformed in all directions, and the conductive clothes 22, 23 are easily deformed with a shift of opposite sides of the sheet-like dielectric body 21, so that a distance between the conductive clothes 22, 23 varies. This varies capacitance of the capacitance-type pressure sensor 2. The frequency components of heart beats and respiration are included in the variations of capacitance.

Because the capacitance-type pressure sensor 2 serves as an oscillation capacitor for the resonant circuit 3, oscillation frequency of the resonant circuit 3 varies with capacitance variations of the capacitance-type pressure sensor 2. The calculation processing circuit 4 detects variations in the oscillation frequency, and calculates the heart rate and/or respiration rate from the frequency component or components of heart beats and/or respiration included in the variations.

In a specific construction of the capacitance-type pressure sensor 2 with one sheet-like dielectric body 21, a plurality of through holes 25 or projections and depressions 26 are formed on the sheet-like dielectric body 21 of the capacitance-type pressure sensor 2. According to the specific construction, the sheet-like dielectric body 21 is easily deformed in all directions when the capacitance-type pressure sensor 2 comes under pressure from the human body, so that a distance between both the conductive clothes 22, 23 sensitively varies in response to the pressure.

Further, in a specific construction of the capacitance-type pressure sensor 2 with two sheet-like dielectric bodies 21, 24, a plurality of through holes 25 or projections and depressions 26 are formed on each of the two sheet-like dielectric bodies 21, 24. The through holes 25 or projections and depressions 26 provided on one sheet-like dielectric body 21 and the through holes 25 or projections and depressions 26 provided on the other sheet-like dielectric body 24 are staggered. According to the specific construction, the two sheet-like dielectric bodies 21, 24 are more easily deformed in all directions when the capacitance-type pressure sensor 2 comes under pressure from the human body, so that a distance between both the conductive clothes 22, 23 more sensitively varies in response to the pressure.

Further, the capacitance-type pressure sensor 2 comprises a pair of conductive clothes 22, 23 with stretchability and flexibility, and a sheet-like dielectric body with stretchability and flexibility provided on at least one of two opposed sides of the pair of conductive clothes. In such a construction, the capacitance-type pressure sensor 2 can be made thinner, so that uncomfortable feeling given to the human body can be reduced.

Furthermore, the capacitance-type pressure sensor 2 comprises a conductive cloth 22 with stretchabliity and flexibility, a conductive plate 33, and a sheet-like dielectric body with stretchabliity and flexibility provided on at least one of two opposed sides of the conductive cloth and conductive plate.

Furthermore, the capacitance-type pressure sensor 2 comprises a pair of conductive clothes 22, 22 with stretchability and flexibility, sheet-like dielectric bodies 27, 27 with stretchability and flexibility provided on two opposed sides of the pair of conductive clothes, a conductive cloth 23 with stretchability and flexibility disposed between the pair of conductive clothes, a connection 22a for electrically connecting the pair of conductive clothes 22, 22 to each other, and a dielectric body 27a with stretchability and flexibility provided on a side of the connection 22a facing the conductive cloth 23.

Furthermore, the capacitance-type pressure sensor 2 comprises a pair of conductive clothes 22, 22 with stretchability and flexibility, a conductive cloth 23 with stretchability and flexibility disposed therebetween, dielectric bodies 28, 29 with stretchability and flexibility provided on opposite sides of the conductive cloth, and a connection 22a for electrically connecting the pair of conductive clothes 22, 22 to each other.

As described above, according to the capacitance-type pressure sensor and the heart beat/respiration measuring device of the invention, the heart rate or respiration rate of the human body can be measured free of restraint and with high accuracy and sensitivity.

BRIEF DESCRIPTION OF THE DRAWINGS

FIG. 8 includes a sectional view for illustrating an elastic deformation state of the capacitance-type pressure sensor;

FIG. 9 includes a sectional view for illustrating an elastic deformation state of another capacitance-type pressure sensor;

DETAILED DESCRIPTION OF THE PREFERRED EMBODIMENTS

Figure 1:
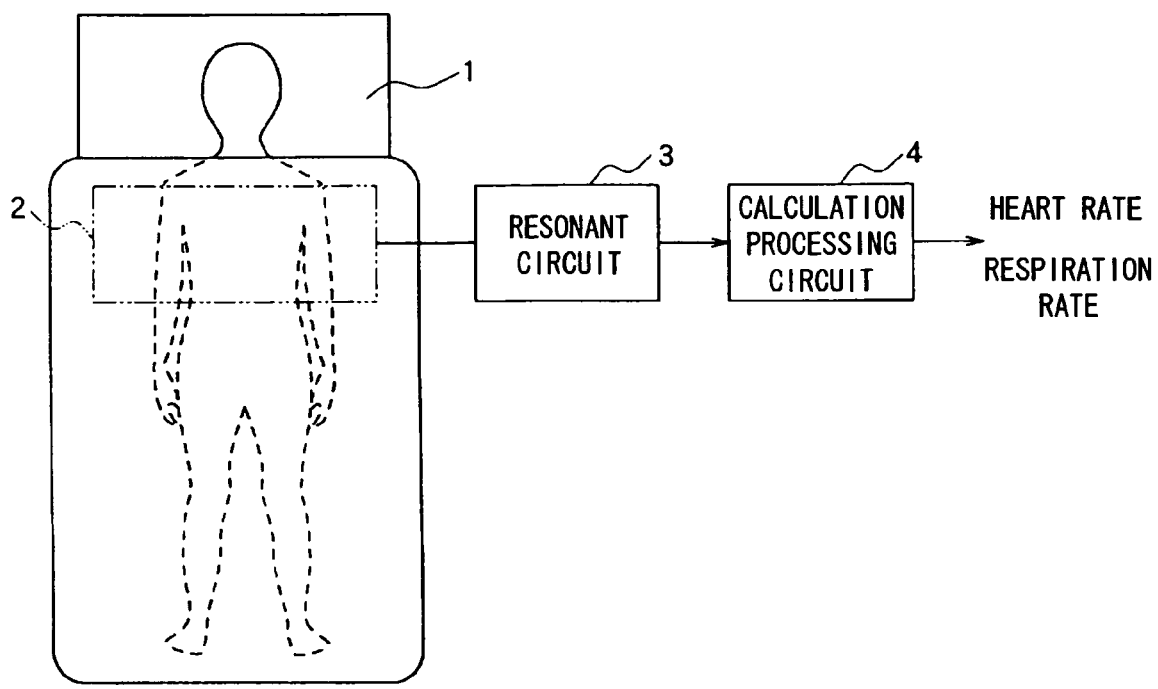
FIG. 1 is a block diagram showing the construction of a heart beat/respiration measuring device embodying the present invention.
Figure 2:
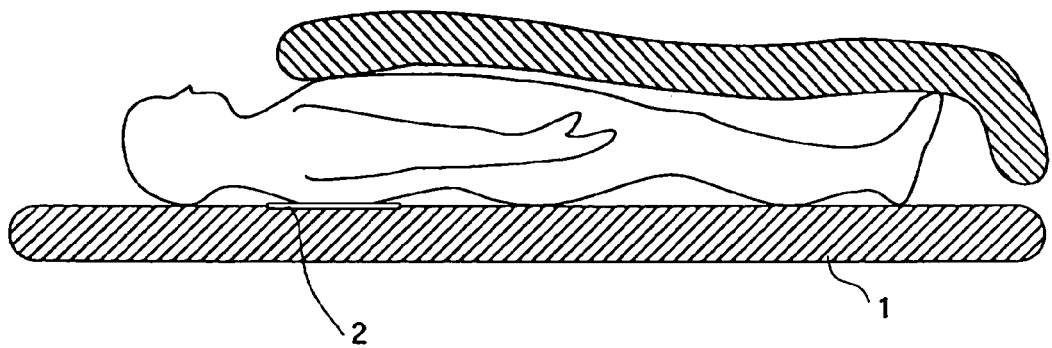
FIG. 2 is a diagram for illustrating the arrangement of a capacitance-type pressure sensor embodying the present invention.
Figure 4:
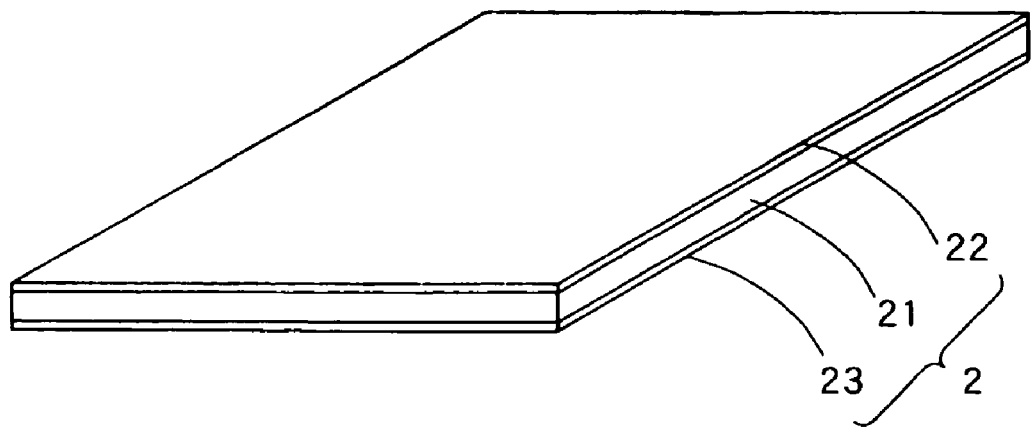
FIG. 4 is a perspective view of the capacitance-type pressure sensor.
Figure 5:
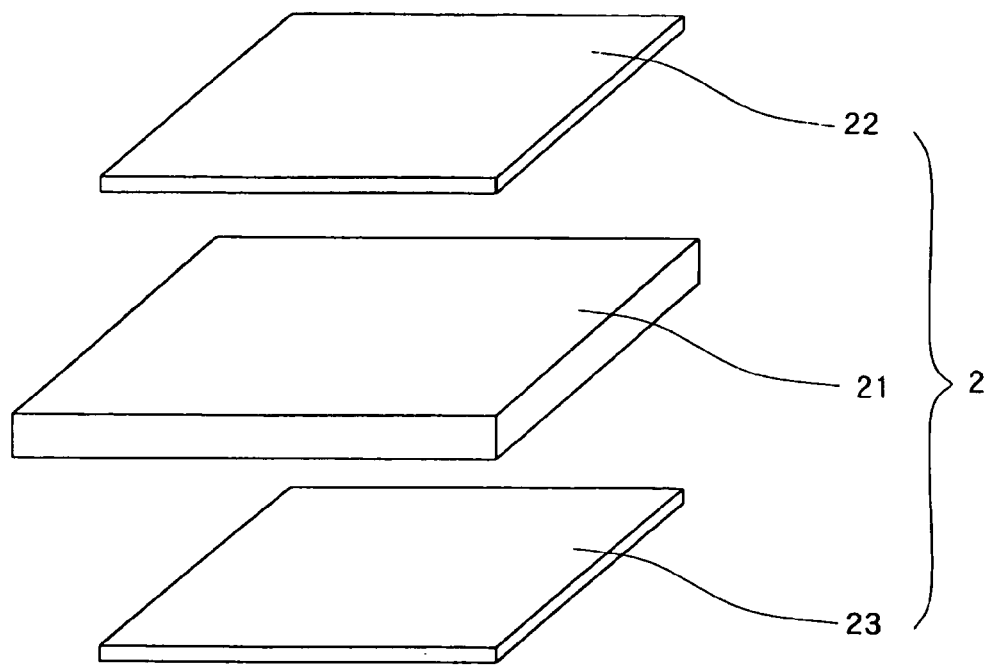
FIG. 5 is an exploded perspective view of the capacitance-type pressure sensor.

Preferred embodiments of the invention will be described below in detail with reference to the drawings. The heart beat/respiration measuring device of the invention comprises a sheet-like capacitance-type pressure sensor 2 disposed on the surface of a mattress 1 for the upper half of the human body as shown in FIGS. 1 and 2. The sensor 2 basically includes a pair of conductive clothes 22, 23 and a sheet-like dielectric body 21 elastic in all directions inserted therebetween, as shown in FIGS. 4 and 5, to constitute a capacitor. The sheet-like sensor 2 may be disposed not only on the surface of the mattress 1 but also inside or on a rear surface of the mattress 1.

The capacitance-type pressure sensor 2 has a size of 50 mm×500 mm, for example. Used for each of the conductive clothes 22, 23 is a highly stretchable material ("SUI-13-55" made by Seiren Co., Ltd., for example). On the other hand, the sheet-like dielectric body 21 is formed of a urethane sheet with a thickness of 3 mm, for example.

The capacitance-type pressure sensor 2 is subjected to pressure fluctuation with the heart beats and respiration of the human body by being pressed against the upper half of the human body lying in a dorsal position, prone position or lateral position as shown in FIGS. 1 and 2. Consequently, the sheet-like dielectric body 21 is elastically deformed not only in a thickness direction but in all directions in accordance with an outer shape of the human body as shown in FIG. 8(a)(b), and the sheet-like dielectric body 21 is easily bent and deformed along a curved surface shape of the human body. As a result, a distance between the conductive clothes 22, 23 on opposite sides varies, so that capacitance of the capacitance-type pressure sensor 2 varies. The frequency components of heart beats and respiration are included in the variations of capacitance.

The capacitance-type pressure sensor 2 may include two sheet-like dielectric bodies 21, 24 elastically deformable not only in a thickness direction but in all directions as shown in FIG. 9(a). The two sheet-like dielectric bodies 21, 24 made of urethane are superposed on each other with one conductive cloth 23 interposed therebetween, and two conductive clothes 22, 22 are disposed respectively on opposite sides of the two sheet-like dielectric bodies 21, 24 with the two conductive clothes 22, 22 electrically connected to each other through a connection 22a.

The capacitance-type pressure sensor 2 is also subjected to pressure from the human body as shown in FIG. 9(b), so that the sheet-like dielectric bodies 21, 24 are elastically deformed not only in a thickness direction but in all directions, and the sheet-like dielectric bodies 21, 24 are easily bent and deformed along a curved surface shape of the human body. As a result, a distance between the intermediate conductive cloth 23 and each of the conductive clothes 22, 22 on opposite sides varies, so that capacitance of the capacitance-type pressure sensor 2 varies. When the two sheet-like dielectric bodies 21, 24 are used, the conductive clothes 22, 22 on the opposite sides may serve as a ground layer to prevent noise.

Figure 6:
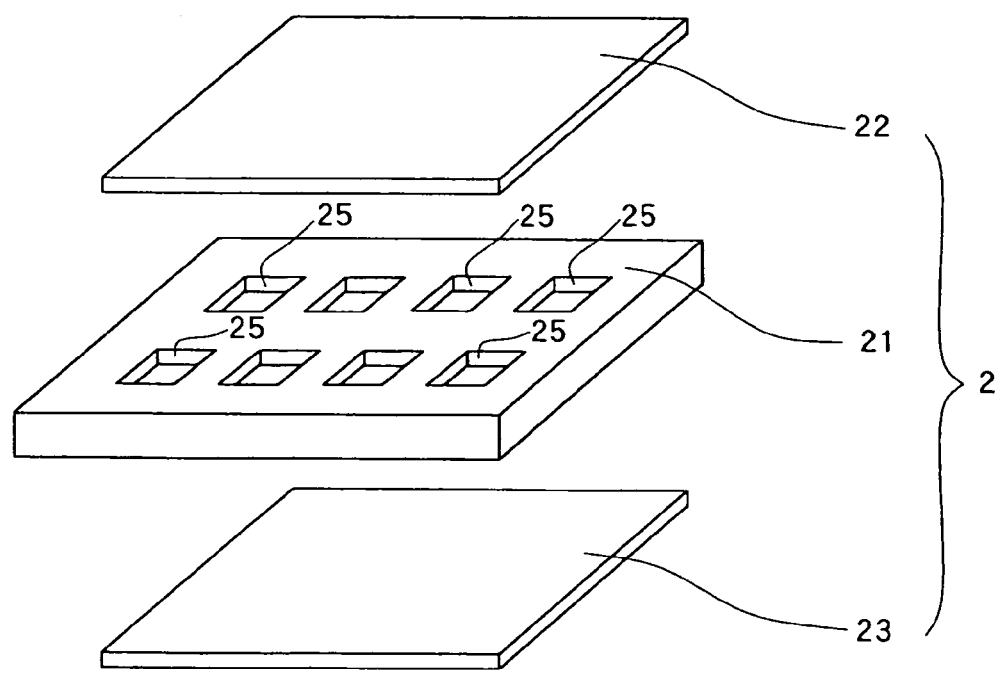
FIG. 6 is an exploded perspective view of another capacitance-type pressure sensor.
Figure 10:
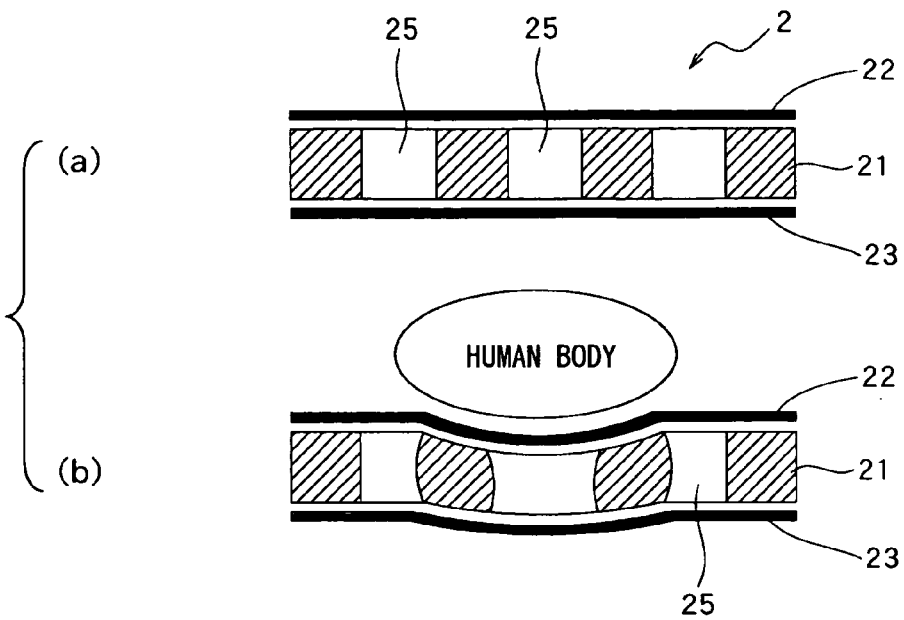
FIG. 10 includes a sectional view for illustrating an elastic deformation state of another capacitance-type pressure sensor.

As further shown in FIGS. 6 and 10(a), a sheet-like dielectric body 21 provided with a plurality of through holes 25 may be used for a capacitance-type pressure sensor 2 using one sheet-like dielectric body 21.

According to the capacitance-type pressure sensor 2, the sheet-like dielectric body 21 is easily deformed not only in a thickness direction but in all directions when coming under pressure from the human body, so that a distance between the two conductive clothes 22, 23 sensitively varies in response to the pressure.

Furthermore, as shown in FIG. 11(a), two sheet-like dielectric bodies 21, 24 each having a plurality of through holes 25 superposed such that the through holes 25 provided on one sheet-like dielectric body 21 and the through holes 25 provided on the other sheet-like dielectric body 24 are staggered may be used for a capacitance-type pressure sensor 2 using two sheet-like dielectric bodies 21, 24. According to the capacitance-type pressure sensor 2, as shown by arrows in FIG. 11(b), the two sheet-like dielectric bodies 21, 24 are more easily deformed not only in a thickness direction but in all directions when coming under pressure from the human body, so that a distance between the both conductive clothes 22, 23 more sensitively varies in response to the pressure.

Furthermore, the capacitance-type pressure sensor 2 may include a pair of conductive clothes 22, 23 with stretchability and flexibility, and sheet-like dielectric bodies 27, 28 with stretchability and flexibility each attached to a whole face of each of two opposed sides of the pair of conductive clothes 22, 23, to provide a pair of sheets 31, 32 in which each of the conductive clothes 22, 23 and each of the sheet-like dielectric bodies 27, 28 are integrated, with the sheet-like dielectric bodies 27, 28 superposed so as to be opposed to each other. In this case, the capacitance-type pressure sensor 2 shown in FIG. 17(a) is different from the capacitance-type pressure sensor 2 shown in FIG. 8 in that separate sheet-like dielectric bodies 27, 28 are each provided on the conductive clothes 22, 23 in place of the sheet-like dielectric body 21 of the capacitance-type pressure sensor 2 shown in FIG. 8.

In such a construction, when in an initial state or in use, these sheets 31, 32 may be in contact with each other in some portions but fail to be in contact in other portions because of stretchability and flexibility thereof as shown in FIG. 17(b). Space occurs in the portions where the sheets 31, 32 fail to be in contact, so that air existing in the space also plays a roll as a dielectric body.

The sheets 31, 32 used for such a capacitance-type pressure sensor 2 have a pair of conductive clothes 22, 23 with a size of 50 mm×500 mm, for example, and a thickness of 0.12 mm. Used for the sheets are vinyl chlorides with a thickness of 0.2 mm bonded as sheet-like dielectric bodies 27, 28 to whole faces of opposed sides of these conductive clothes ("KTS-70" made by Seiren Co., Ltd., for example).

When such a capacitance-type pressure sensor 2 is subjected to pressure against a curved surface of the human body as shown in FIG. 17(c), stretchability and flexibility of the sheets 31, 32 cause flexures. Variations in a distance and location of the flexures due to respiration of the human body vary a location and size of space between the sheets 31, 32, so that capacitance of the capacitance-type pressure sensor 2 varies. The capacitance-type pressure sensor 2 described above can be made thinner, so that uncomfortable feeling given to a user can be reduced.

Figure 18:
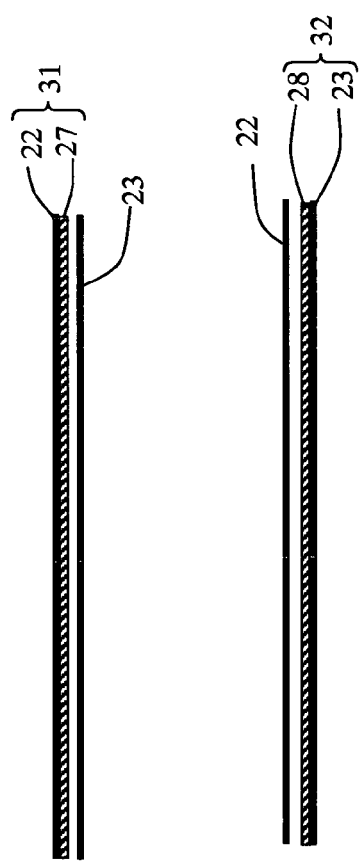
FIG. 18 includes sectional views showing two other construction examples of the capacitance-type pressure sensor.

Further, as shown in FIG. 18(a), the capacitance-type pressure sensor 2 may include a pair of conductive clothes 22, 23 with stretchability and flexibility, and a sheet-like dielectric body 27 with stretchability and flexibility attached to only one conductive cloth 22 of the two conductive clothes at a side thereof opposed to the other, to provide an integrated sheet 31. Furthermore, as shown in FIG. 18(b), the capacitance-type pressure sensor 2 may include a pair of conductive clothes 22, 23 with stretchablity and flexibility, and a sheet-like dielectric body 28 with stretchability and flexibility attached to only one conductive cloth 23 of the two conductive clothes at a side thereof opposed to the other, to provide an integrated sheet 32.

Figure 17:
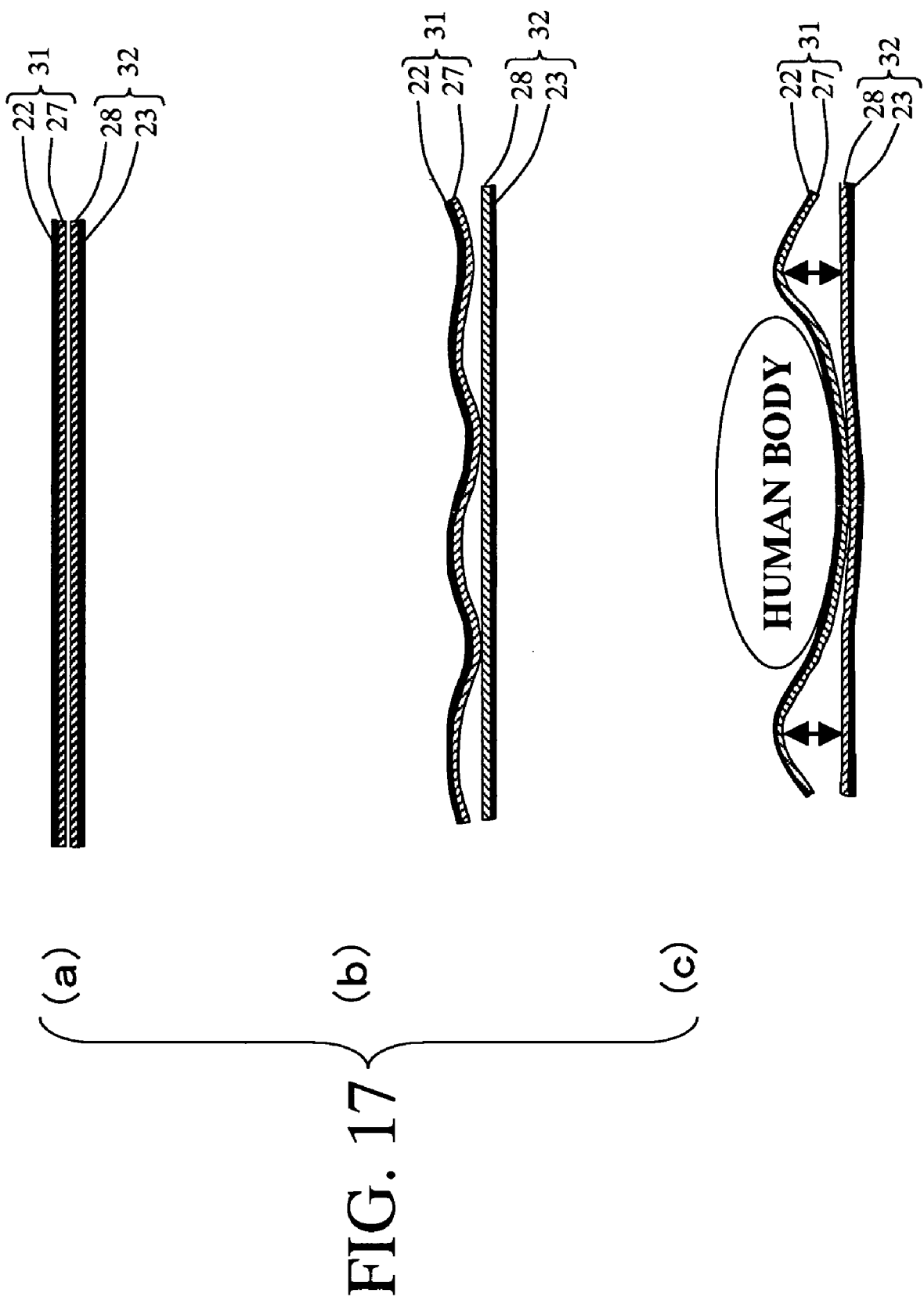
FIG. 17 includes sectional views for illustrating elastic deformation states of another capacitance-type pressure sensor.

When the capacitance-type pressure sensor 2 of FIG. 18(a) is in an initial state or in use, like the capacitance-type pressure sensor 2 shown in FIG. 17, the sheet 31 and the conductive cloth 23 may be in contact with each other in some portions but fail to be in contact in other portions. In this case, the human body is to be positioned on the conductive cloth 22.

Further, when the capacitance-type pressure sensor 2 of FIG. 18(b) is in an initial state or in use, the conductive cloth 22 and the sheet 32 may be in contact with each other in some portions but fail to be in contact in other portions. In this case also, the human body is to be positioned on the conductive cloth 22.

Figure 19:
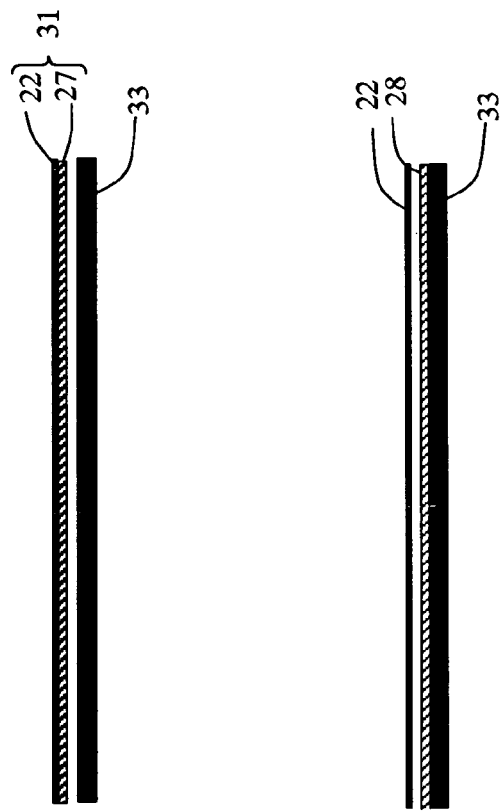
FIG. 19 includes sectional views showing two still other construction examples of the capacitance-type pressure sensor.

Further, as shown in FIG. 19(a), the capacitance-type pressure sensor 2 may include a conductive cloth 22 with stretchability and flexibility and a conductive plate 33 such as a copper plate as a pair of electrodes, and further include a sheet-like dielectric body 27 with stretchability and flexibility attached to the conductive cloth 22. As shown in FIG. 19(b), a sheet-like dielectric body 28 with stretchability and flexibility may be attached to the conductive plate 33. In both the cases of FIGS. 19(a) and 19(b), the human body is to be positioned on the conductive cloth 22.

Furthermore, as shown in FIG. 20(a), the capacitance-type pressure sensor 2 may include a pair of conductive clothes 22, 22 with stretchability and flexibility, sheet-like dielectric bodies 27, 27 with stretchability and flexibility each attached to each of two opposed sides of the conductive clothes to provide a pair of sheets 31, 31 in which each of the conductive clothes 22, 22 and each of the sheet-like dielectric bodies 27, 27 are integrated, a conductive cloth 23 with stretchability and flexibility disposed between these sheets 31, 31 superposed such that the sheet-like dielectric bodies 27, 27 are opposed to each other, a connection 22a for electrically connecting the pair of conductive clothes 22, 22 to each other, and a dielectric body 27a with stretchability and flexibility attached to a side of the connection 22a facing the conductive cloth 23 to provide an integrated connecting sheet 34.

In this case, when in an initial state or in use, these opposed sheets 31, 31 and the connecting sheet 34 may be in contact with the conductive cloth 23 in some portions but fail to be in contact with the conductive cloth 23 in other portions between each of the opposed sheets 31, 31 and the conductive cloth 23 and between the integrated connecting sheet 34 and the conductive cloth 23 because of stretchability and flexibility thereof as shown in FIG. 20(b). Space occurs in the portions where the sheets 31, 31 and the connecting sheet 34 fail to be in contact with the conductive cloth 23, so that air existing in the space also plays a roll as a dielectric body.

Figure 20:
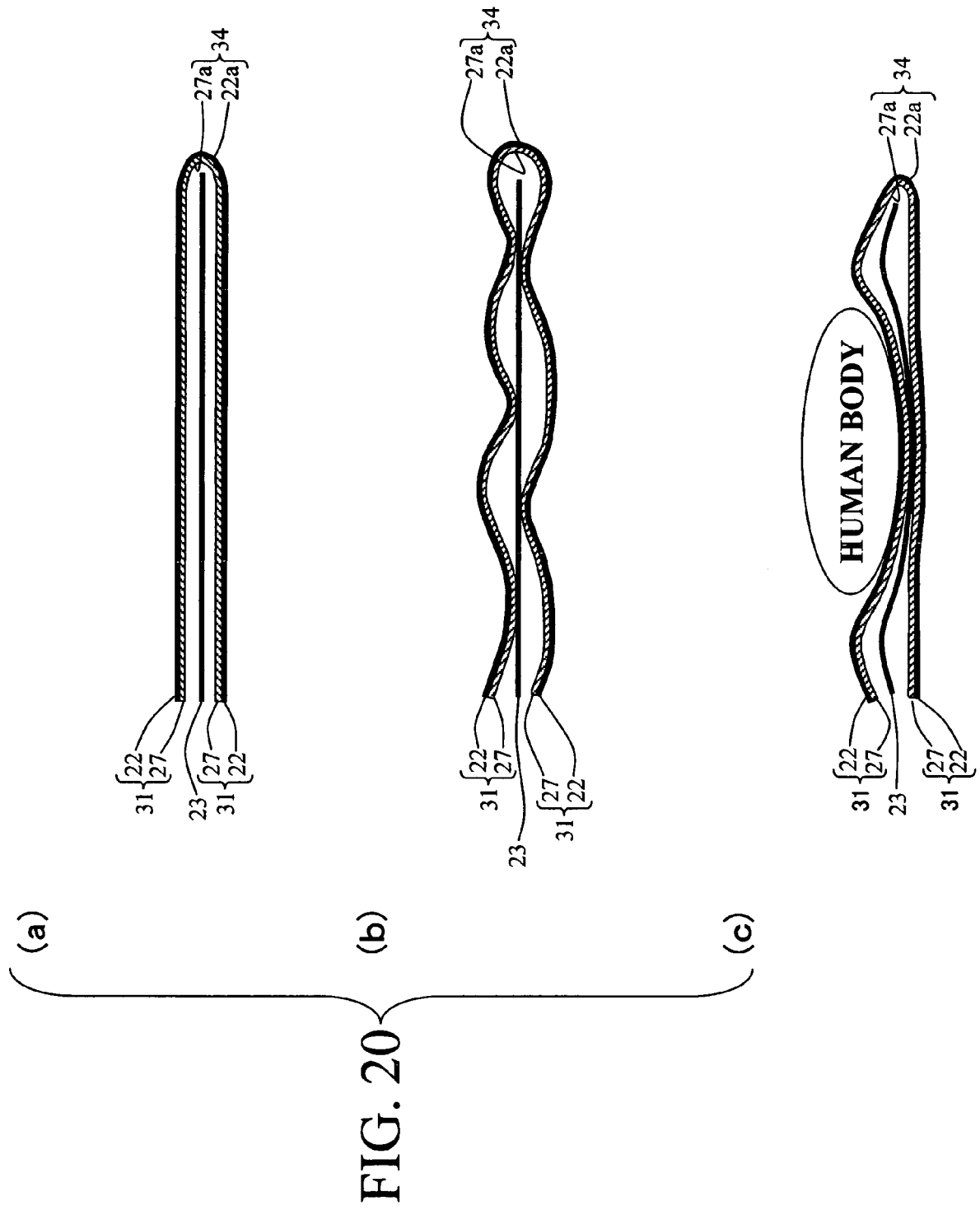
FIG. 20 includes sectional views for illustrating elastic deformation states of another capacitance-type pressure sensor.

When such a capacitance-type pressure sensor 2 is subjected to pressure against the human body as shown in FIG. 20(*c*), stretchablity and flexibility of the sheets 31, 31, the connecting sheet 34, and the conductive cloth 23 cause flexures. Variations in a distance and location of the flexures due to respiration of the human body vary a location and size of space between the sheets 31, 31 and the connecting sheet 34, and the conductive cloth 23, so that capacitance of the capacitance-type pressure sensor 2 varies.

In such a construction, in order for the conductive cloth 23 not to be in contact with the conductive clothes 22, 22 and the connection 22*a*, the sheet-like dielectric bodies 27, 27 and the dielectric body 27*a* are connected so as to be successively integrated with no space therebetween, for example. The present embodiment provides the sheets 31, 31 and the connecting sheet 34 by folding a sheet integratedly formed of a conductive cloth and sheet-like dielectric body.

Figure 21:
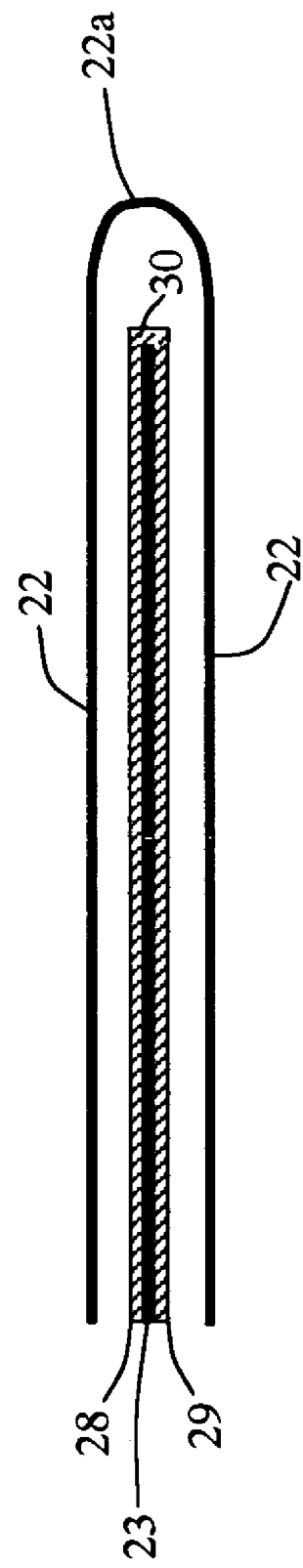
FIG. 21 is a sectional view showing another construction example of the capacitance-type pressure sensor.

Furthermore, as shown in FIG. 21, the capacitance-type pressure sensor 2 may include a pair of opposed conductive clothes 22, 22, a conductive cloth 23 with stretchability and flexibility disposed therebetween, dielectric bodies 28, 29 with stretchability and flexibility attached to opposite sides of the conductive cloth, a dielectric body 30 with stretchability and flexibility attached to an end face of the conductive cloth, and a connection 22*a* for electrically connecting the pair of conductive clothes 22, 22 to each other. The present embodiment provides the pair of conductive clothes 22, 22 and the connection 22*a* by folding a conductive cloth.

As shown in FIG. 1, the capacitance-type pressure sensor 2 has connected thereto a resonant circuit 3 wherein the sensor 2 serves as an oscillation capacitor. Further connected to the resonant circuit 3 is a calculation processing circuit 4 comprising a microcomputer etc.

Figure 3:
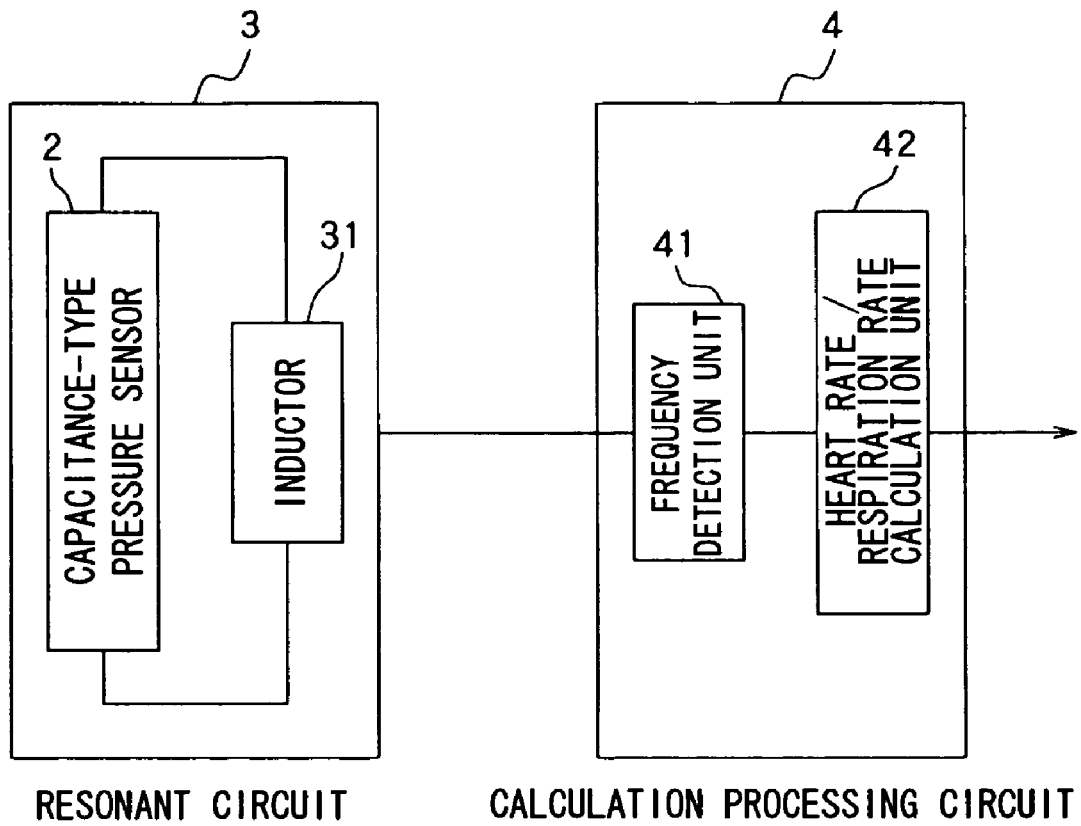
FIG. 3 is a block diagram showing the construction of a resonant circuit and a calculation processing circuit.

The resonant circuit 3 may be an LC oscillation circuit including an inductor 31 connected to the capacitance-type pressure sensor 2 as shown in FIG. 3, for example. Furthermore, the calculation processing circuit 4 includes a frequency detection unit 41 for detecting variations in the oscillation frequency of the resonant circuit 3 and a heart rate/respiration rate calculation unit 42 for calculating a heart rate and/or respiration rate based on the frequency component or components of heart beats and/or respiration included in the variations in the oscillation frequency.

Figure 7:
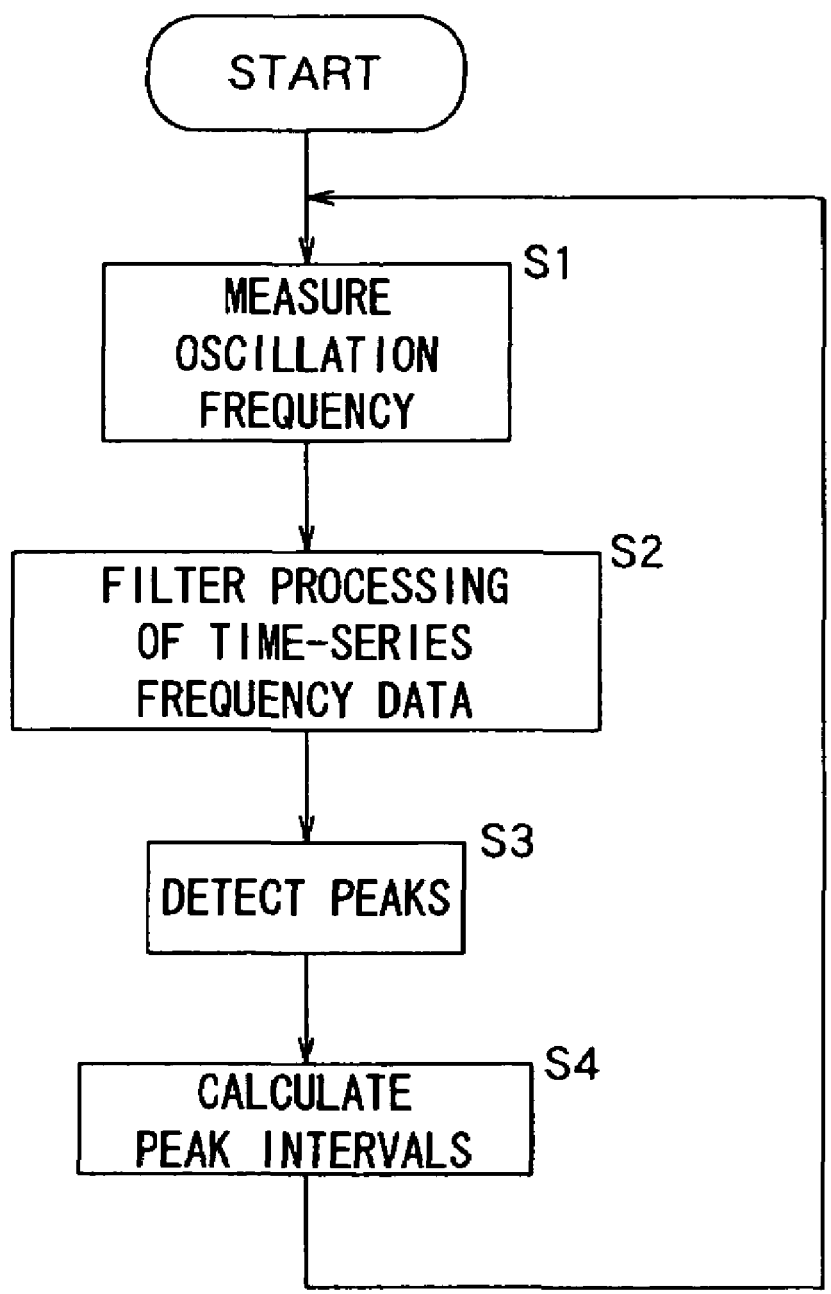
FIG. 7 is a flow chart for illustrating the operation of the calculation processing circuit.

The resonant circuit 3 produces a voltage signal of rectangular waveform, which is fed to the calculation processing circuit 4. With reference to FIG. 7, the calculation processing circuit 4 first measures a frequency (an oscillation frequency) in step S1 by counting the number of pulses of the voltage signal of rectangular waveform by a counter incorporated in the circuit. Variations in the measured value indicate variations in capacitance of the capacitance-type pressure sensor 2. The variations in the capacitance include the frequency components of heart beats and respiration. The oscillation frequency may be measured not only by counting the number of pulses at regular time intervals (50 msec., for example), but by measuring a period of time during which the number of pulses reaches a given value.

The variation in the oscillation frequency (time-series frequency data) is subjected to calculation processing as by a digital filter next in step S2. Here, filter processing extracts the variation component of heart beats and the variation component of respiration from the variation component of capacitance of the capacitance-type pressure sensor 2. Peaks of the time-series frequency data subjected to the filter processing are detected subsequently in step S3. Intervals of the detected peaks are calculated, and further the heart rate and the respiration rate are calculated from the result finally in step S4.

Figure 11:
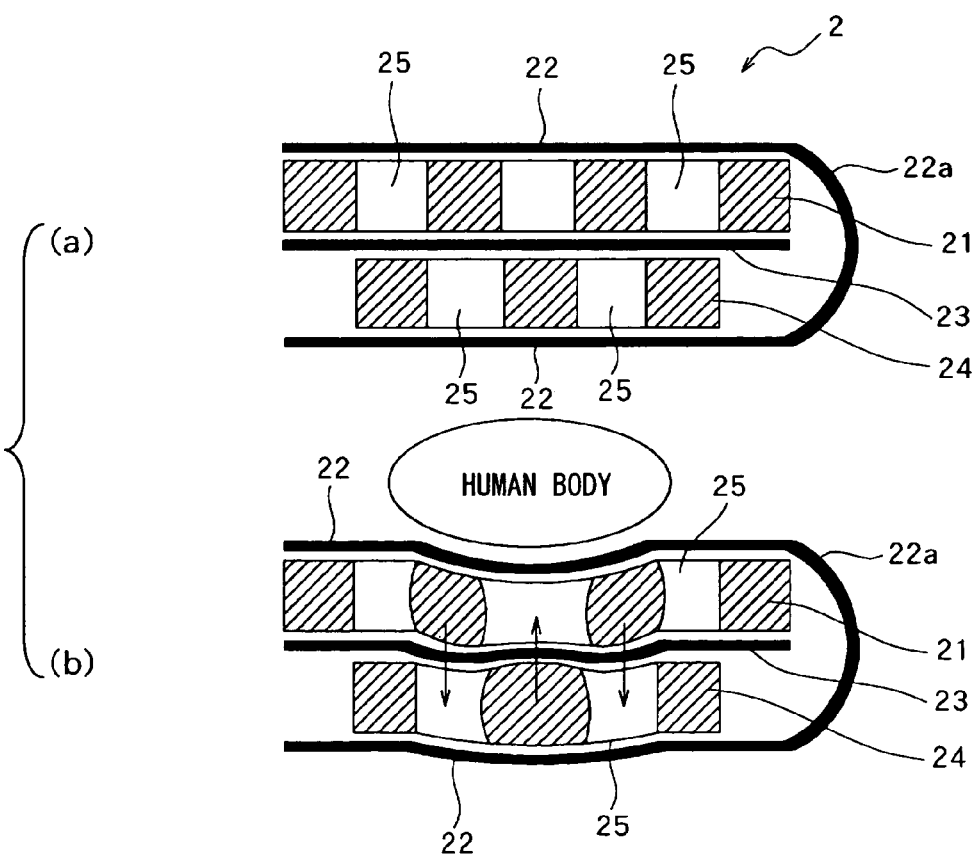
FIG. 11 includes a sectional view for illustrating an elastic deformation state of still another capacitance-type pressure sensor.
Figure 12:
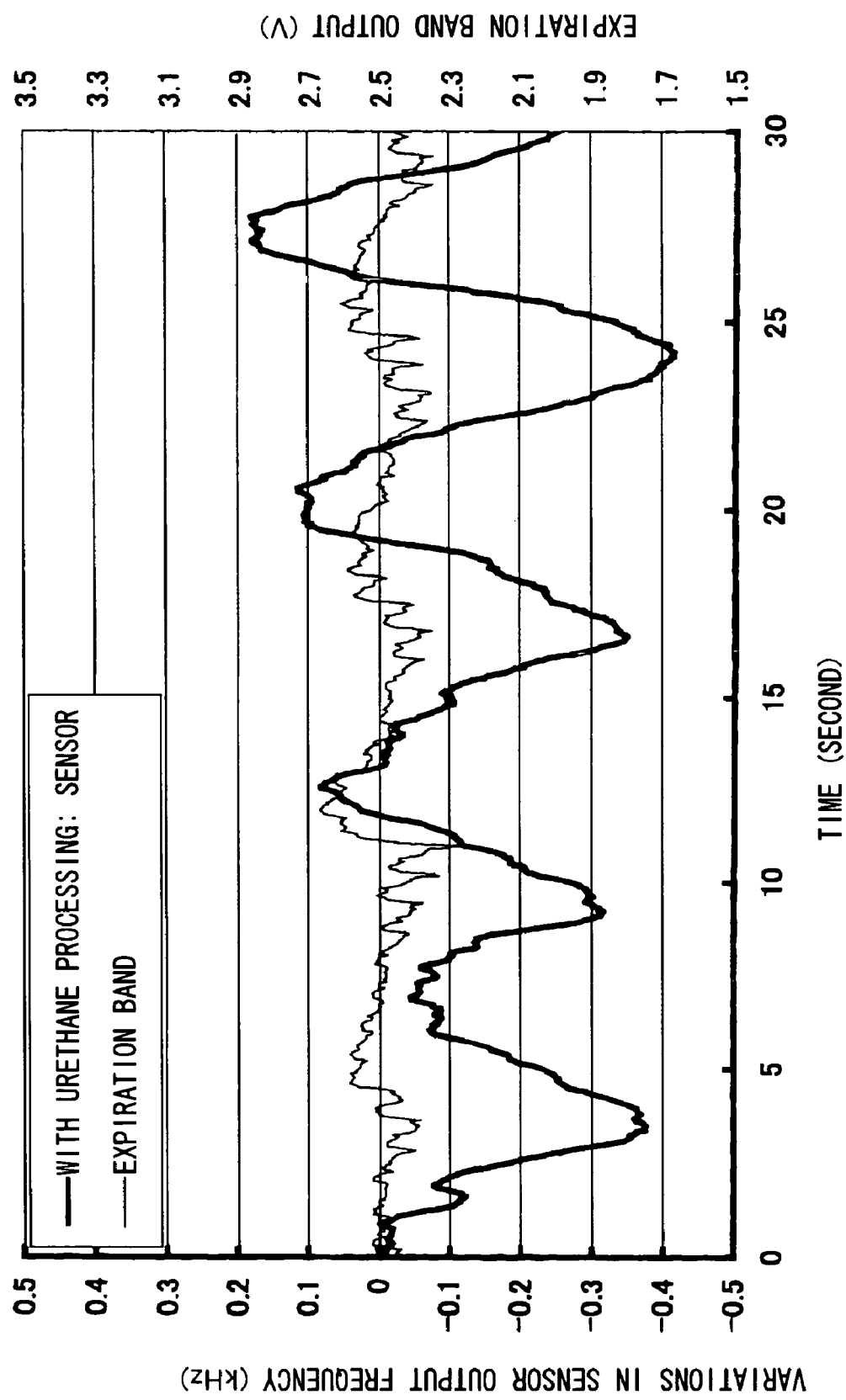
FIG. 12 is a graph showing variations in the oscillation frequency as measured by the capacitance-type pressure sensor of the present invention and variations in the output of an expiration band.
Figure 13:
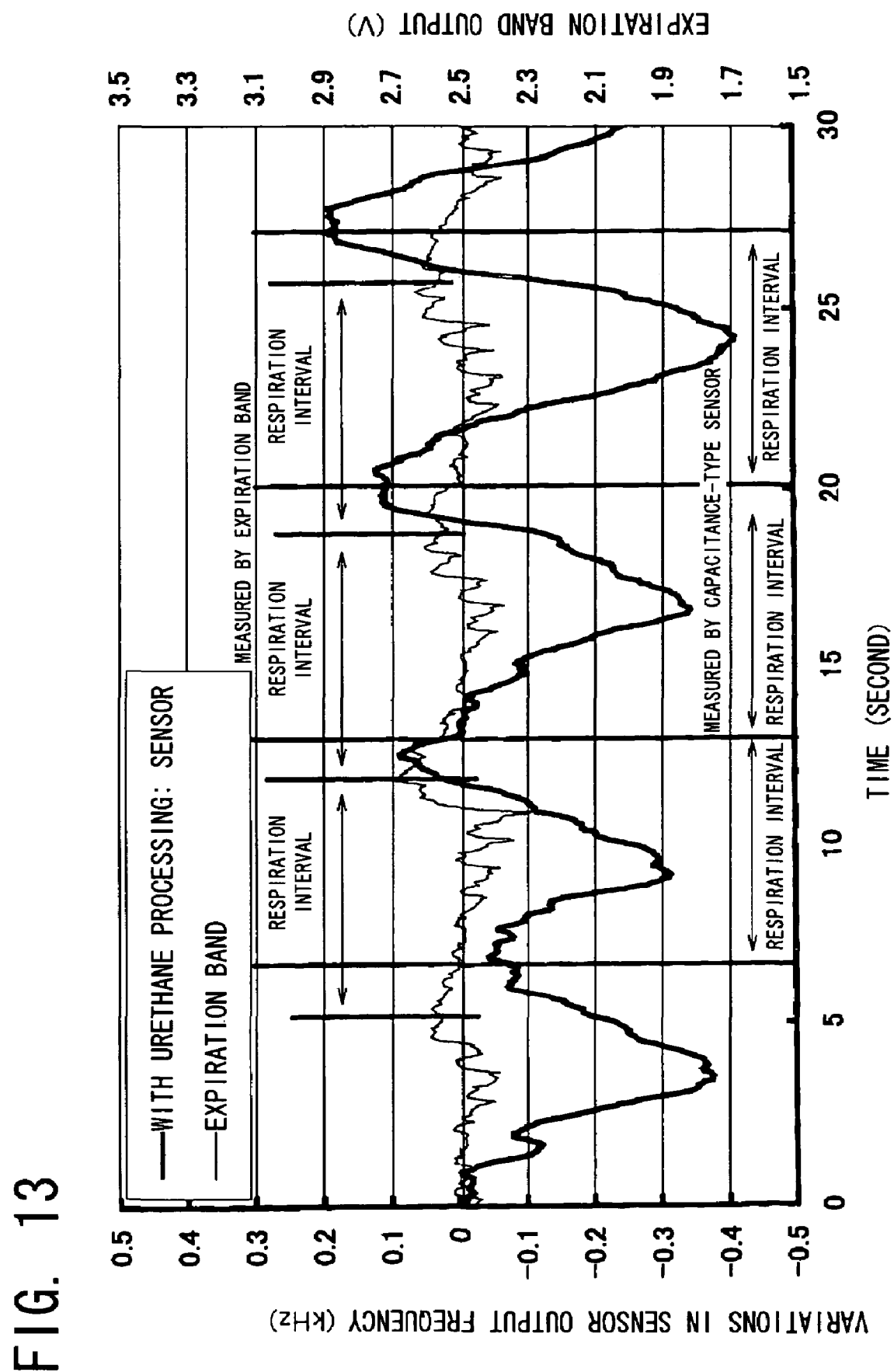
FIG. 13 is a graph in which respiration intervals are entered in the graph of FIG. 12.

A graph of FIG. 12 shows variations in the oscillation frequency as measured by the capacitance-type pressure sensor 2 of the present invention shown in FIG. 11 and variations in the output of a respiration sensor using a conventional expiration band. FIG. 13 is a graph in which respiration intervals as measured by the expiration band and respiration intervals as measured by the capacitance-type pressure sensor are entered in the same graph. Because these two respiration intervals are approximately consistent, the capacitance-type pressure sensor 2 of the present invention can be said to have sufficiently high accuracy.

A phase difference exists between the variations in the oscillation frequency as measured by the capacitance-type pressure sensor of the present invention and the variations in the output of the pressure sensor using the conventional expiration band mainly because of a delay due to filtering etc.

Figure 14:
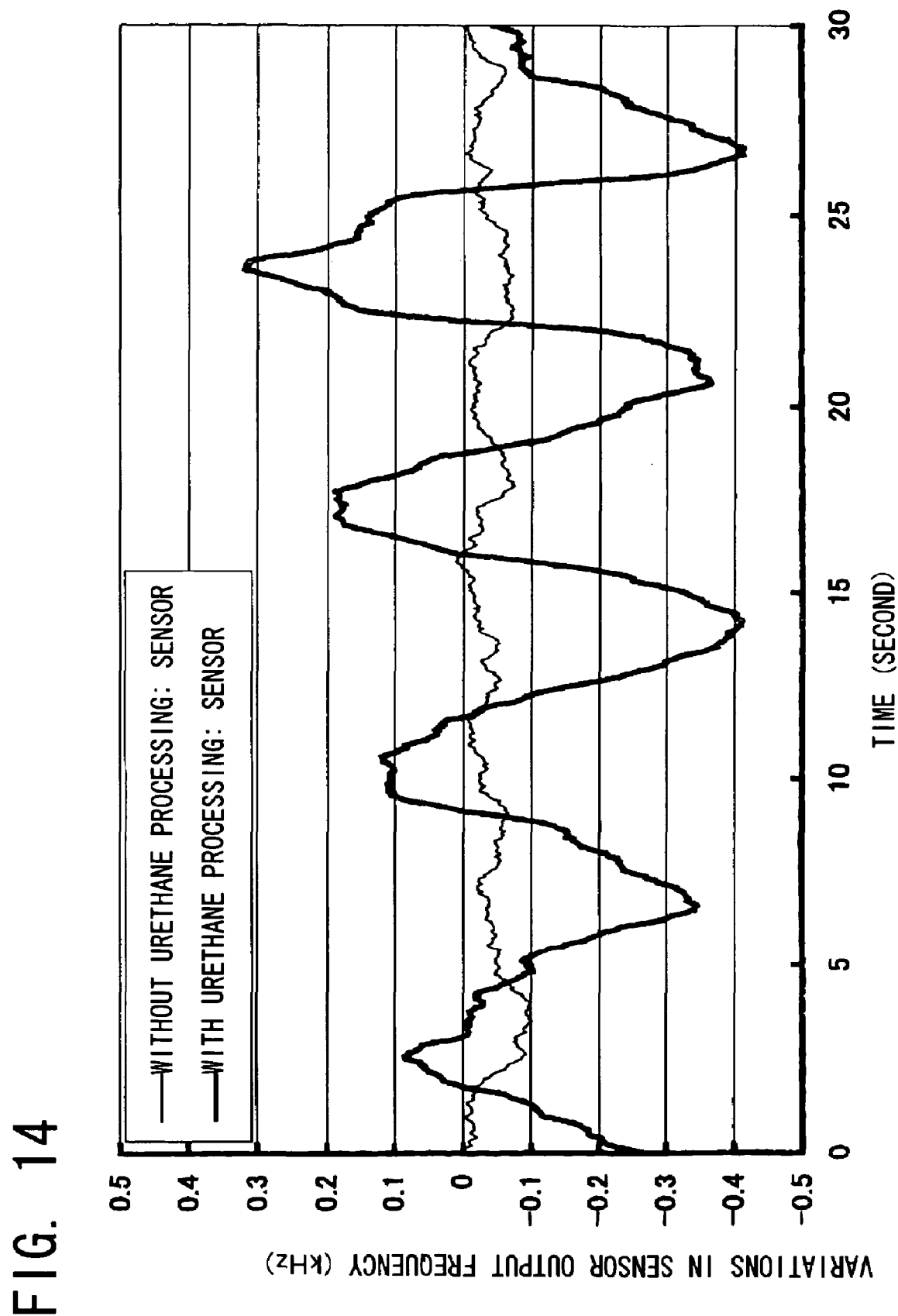
FIG. 14 is a graph in which variations in the oscillation frequency as measured by a capacitance-type pressure sensor without urethane processing and variations in the oscillation frequency as measured by a capacitance-type pressure sensor with urethane processing are compared.

FIG. 14 shows variations in the oscillation frequency of a capacitance-type pressure sensor in which sheet-like dielectric bodies 21, 24 made of urethane are not processed (without urethane processing) as shown in FIG. 9 and a capacitance-type pressure sensor in which sheet-like dielectric bodies 21, 24 made of urethane are processed to have through holes 25 (with urethane processing) as shown in FIG. 11. Greater amplitude is obtained in the capacitance-type pressure sensor in which sheet-like dielectric bodies are not processed (without urethane processing) than in the capacitance-type pressure sensor in which sheet-like dielectric bodies are processed to have through holes (with urethane processing) as illustrated. Therefore, it can be said that processing sheet-like dielectric bodies to make through holes allows detection of pressure variations with higher accuracy.

Figure 15:
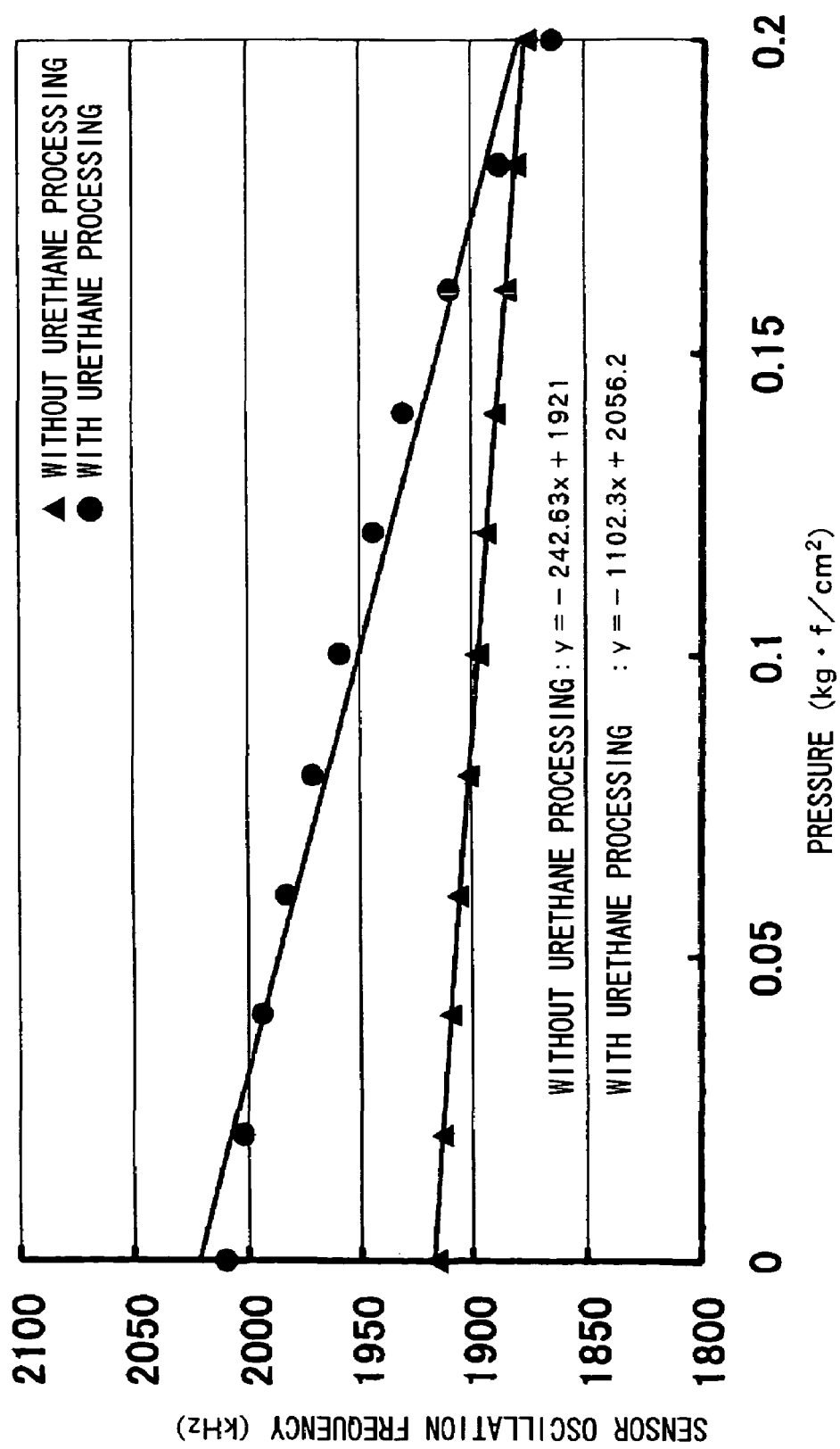
FIG. 15 is a graph in which variations in the oscillation frequency to pressure of the capacitance-type pressure sensor without urethane processing and the capacitance-type pressure sensor with urethane processing are compared.
Figure 16:
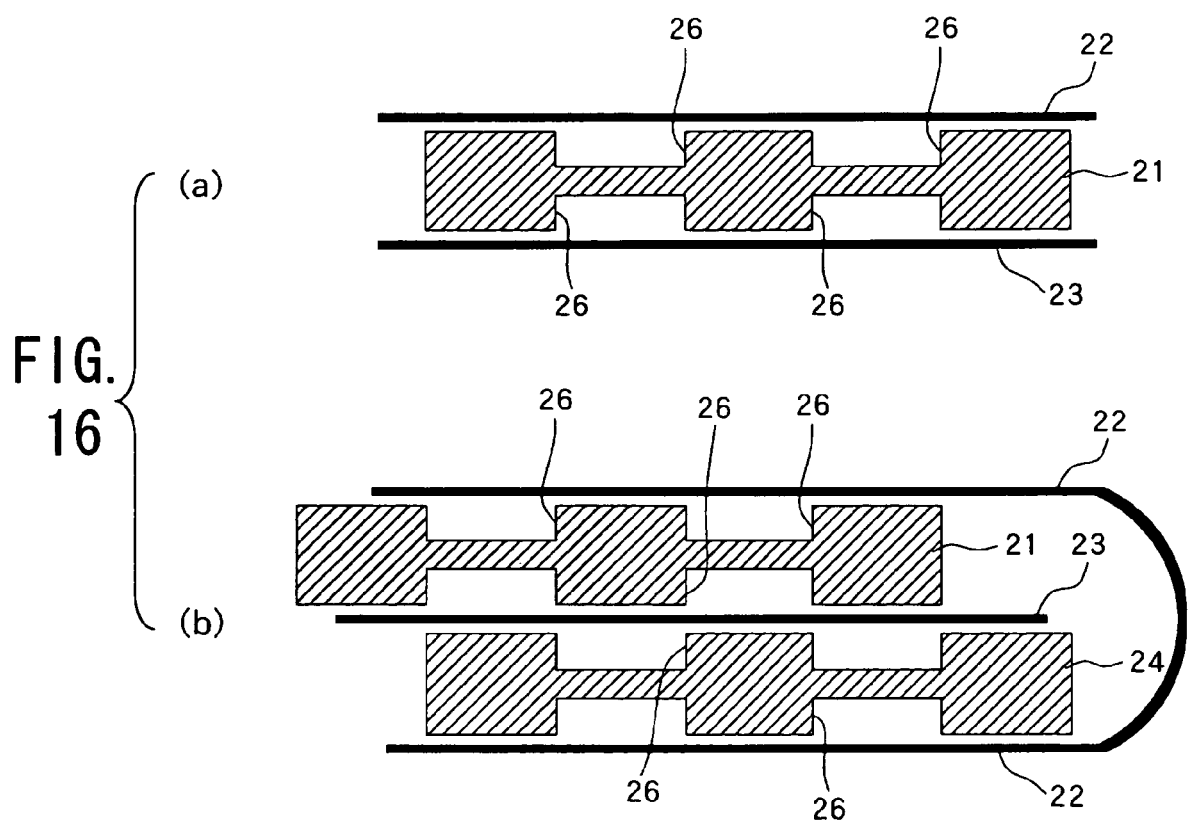
FIG. 16 includes sectional views showing other construction examples of the capacitance-type pressure sensor embodying the present invention.

A graph of FIG. 15 further shows a relationship between pressure and oscillation frequency in the capacitance-type pressure sensor without urethane processing and the capacitance-type pressure sensor with urethane processing. The capacitance-type pressure sensor with urethane processing has greater variations in frequency to pressure than the capacitance-type pressure sensor without urethane processing as illustrated.

Because pressure that acts on the capacitance-type pressure sensor 2 from the human body is in the range of approximately 0.05 to 0.15 Kgf/cm$^2$, the capacitance-type pressure sensor with urethane processing can measure the heart rate and respiration rate with higher sensitivity than the capacitance-type pressure sensor without urethane processing.

Figure 22:
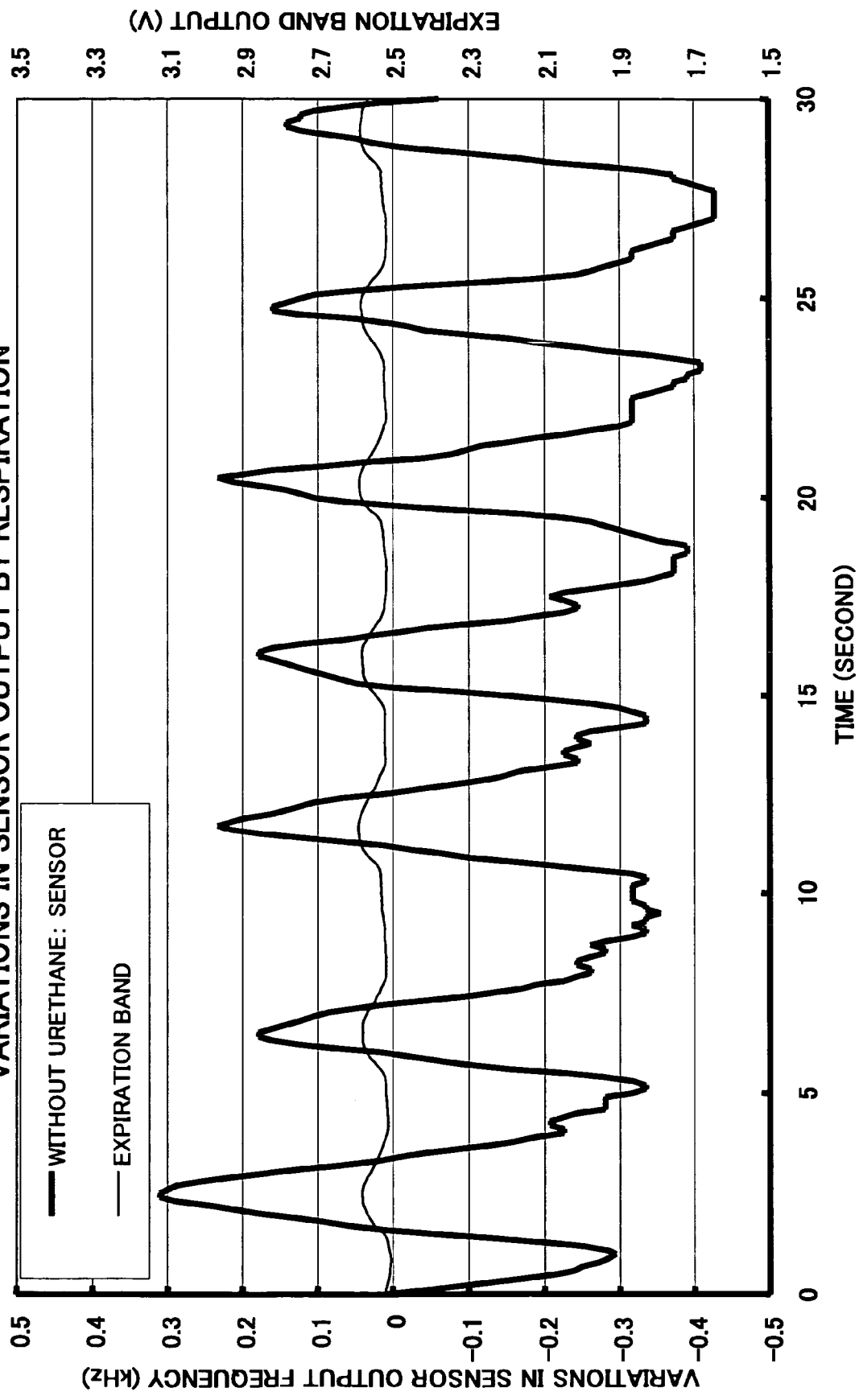
FIG. 22 is a graph showing variations in the oscillation frequency as measured by the capacitance-type pressure sensor shown in FIG. 17 and variations in the output of the expiration band.

A graph of FIG. 22 shows variations in the oscillation frequency as measured by the capacitance-type pressure sensor 2 of the present invention shown in FIG. 17(*a*)(*b*) and variations in the output of a respiration sensor using a conventional expiration band. Because these two respiration intervals are approximately consistent, the capacitance-type pressure sensor 2 of the present invention can be said to have sufficiently high accuracy.

As described above, in the case of the heart beat/respiration measuring device of the present invention, the sensor 2 can be attached to the mattress 1, so that the heart rate and respiration rate of the human body in a recumbent position can be measured without restraining the human body. With the device of the present invention, the capacitance-type pressure sensor 2 is used in which conductive clothes are disposed on opposite sides of a sheet-like dielectric body as described above, with the result that the heart rate and respiration rate can be calculated with high accuracy and sensitivity.

The device of the present invention is not limited to the foregoing embodiments in construction but can be modified variously by one skilled in the art without departing from the spirit of the invention as set forth in the appended claims. For example, the through holes 25 to be provided on the sheet-like dielectric body 21 shown in FIG. 6 are not limited to square holes but may be round holes.

Further, in place of the sheet-like dielectric bodies 21, 24 provided with a plurality of through holes 25 shown in FIGS. 8 and 9, the sheet-like dielectric bodies 21, 24 having a plurality of projections and depressions 26 formed thereon also can obtain similar effect.

Furthermore, as shown in FIGS. 9, 11, 16(b), 20, and 21, the embodiments of the present invention use capacitance-type pressure sensors of two-layer structure, but those with other multi-layer structures such as three-layer and four-layer structures may be also used. This varies a distance between conductive clothes more sensitively in response to pressure exerted by a curved surface of the human body, so that the heart rate and respiration rate can be calculated with higher accuracy and sensitivity.

The embodiments described use sheet-like dielectric bodies with elasticity or those with elasticity, stretchability, and flexibility, but those with only stretchability and flexibility may be also used. The dielectric bodies of the embodiments of the present invention include insulators.

What is claimed is:

1. A capacitance-type pressure sensor comprising two sheet-like dielectric bodies elastically deformable in all directions superposed on each other with one conductive cloth interposed therebetween, and two conductive clothes disposed on opposite sides of the two sheet-like dielectric bodies stacked together, the two conductive clothes being electrically connected to each other, wherein a plurality of through holes or projections and depressions are formed on each of the two sheet-like dielectric bodies, and the through holes or projections and depressions provided on one sheet-like dielectric body and the through holes or projections and depressions provided on the other sheet-like dielectric body are staggered.

2. A heart beat/respiration measuring device comprising:
a sheet-like capacitance type pressure sensor adapted to be pressed against a human body, and
a measuring circuit for measuring a heart rate and/or respiration rate from the output of the sensor, the capacitance-type pressure sensor comprising:
two sheet-like dielectric body elastically deformable in all directions superposed on each other with one conductive cloth interposed therebetween, and
two conductive clothes with stretchability disposed on opposite sides of the two dielectric body stacked together, the two conductive clothes being electrically connected to each other, the measuring circuit comprising:
a resonant circuit wherein the capacitance-type pressure sensor serves as an oscillation capacitor, and
a calculation processing circuit for detecting variations in the oscillation frequency of the resonant circuit and calculating the heart rate and/or respiration rate based on the frequency component or components of the heart beats and/or respiration included in the variations, wherein,
a plurality of through holes or projections and depressions are formed on each of the two sheet-like dielectric bodies, and the through holes or projections and depressions provided on one sheet-like dielectric body and the through holes or projections and depressions provided on the other sheet-like dielectric body are staggered.

3. A capacitance-type pressure sensor comprising a first conductive cloth with stretchability and flexibility, a second conductive cloth with stretchability and flexibility opposed to the first conductive cloth, and a sheet-like dielectric body with stretchability and flexibility provided on the side of the first conductive cloth opposed to the second conductive cloth, wherein the sensor has space between the second conductive cloth and the sheet-like dielectric body, and a location and size of the space varies a capacitance of the capacitance-type pressure sensor.

4. The heart beat/respiration measuring device comprising:
the capacitance-type pressure sensor according to claim 3, adapted to be pressed against a human body, and
a measuring circuit for measuring a heart rate and/or respiration rate from the output of the sensor, wherein the measuring circuit comprises:
a resonant circuit wherein the capacitance-type pressure sensor serves as an oscillation capacitor, and
a calculation processing circuit for detecting variations in the oscillation frequency of the resonant circuit and calculating the heart rate and/or respiration rate based on the frequency component or components of heart beats and/or respiration included in the variations.

5. A capacitance-type pressure sensor comprising:
a first conductive cloth with stretchability and flexibility;
a second conductive cloth with stretchability and flexibility opposed to the first conductive cloth;
a first sheet-like dielectric body with stretchability and flexibility provided on the side of the first conductive cloth opposed to the second conductive cloth;
a second sheet-like dielectric body with stretchability and flexibility provided on the side of the second conductive cloth opposed to the first conductive cloth, and
a third conductive cloth with stretchability and flexibility provided between the first sheet-like dielectric body and the second sheet-like dielectric body, wherein
the sensor has a space at least either between the third conductive cloth and the first sheet-like dielectric body or between the third conductive cloth and the second sheet-like dielectric body, and
a location and a size of the space varies a capacitance of the capacitance-type pressure sensor.

6. A heart beat/respiration measuring device comprising the capacitance-type pressure sensor according to claim 5, adapted to be pressed against a human body, and
a measuring circuit for measuring a heart rate and/or respiration rate from the output of the sensor, the measuring circuit comprising
a resonant circuit, wherein the capacitance-type pressure sensor serves as an oscillation capacitor, and
a calculation processing circuit for detecting variations in the oscillation frequency of the resonant circuit and calculating the heart rate and/or respiration rate based on the frequency component or components of heart beats and/or respiration included in the variations.

7. A capacitance-type pressure sensor comprising:
a first conductive cloth with stretchability and flexibility;
a second conductive cloth with stretchability and flexibility opposed to the first conductive cloth;
a third conductive cloth with stretchability and flexibility provided between the first conductive cloth and the second conductive cloth;
a first sheet-like dielectric body with stretchability and flexibility provided on the side of the third conductive cloth opposed to the first conductive cloth, and a second sheet-like dielectric body with stretchability and flexibility provided on the side of the third conductive cloth opposed to the second conductive cloth, wherein the sensor has a space at least either between the first sheet-like dielectric body and the first conductive cloth or between the second sheet-like dielectric body and the second conductive cloth, and a location and a size of the space varies a capacitance of the capacitance-type pressure sensor.

8. A heart beat/respiration measuring device comprising the capacitance-type pressure sensor according to claim 7, adapted to be pressed against a human body, and a measuring circuit for measuring a heart rate and/or respiration rate from the output of the sensor, the measuring circuit comprising a resonant circuit, wherein said capacitance-type pressure sensor serves as an oscillation capacitor, and a calculation processing circuit for detecting variations in the oscillation frequency of the resonant circuit and calculating the heart rate and/or respiration rate based on the frequency component or components of heart beats and/or respiration included in the variations.

9. A capacitance-type pressure sensor comprising a conductive cloth with stretchability and flexibility, a conductive plate opposed to the conductive cloth, and a sheet-like dielectric body with stretchability and flexibility provided on the side of the conductive cloth opposed to the conductive plate, wherein the sensor has a space between the dielectric body and the conductive plate, and a location and a size of the space varies a capacitance of the capacitance-type pressure sensor.

10. A capacitance-type pressure sensor comprising a conductive cloth with stretchability and flexibility, a conductive plate opposed to the conductive cloth, and a sheet-like dielectric body with stretchability and flexibility provided on the side of the conductive plate opposed to the conductive cloth, wherein the sensor has a space between the dielectric body and the conductive cloth, and a location and size of the space varies a capacitance of the capacitance-type pressure sensor.

11. A heart beat/respiration measuring device comprising:

the capacitance-type pressure sensor according to either claim 9 or 10, adapted to be pressed against a human body, and a measuring circuit for measuring a heart rate and/or respiration rate from the output of the sensor, wherein the measuring circuit comprises:

a resonant circuit, wherein the capacitance-type pressure sensor serves as an oscillation capacitor, and a calculation processing circuit for detecting variations in the oscillation frequency of the resonant circuit and calculating the heart rate and/or respiration rate based on the frequency component or components of heart beats and/or respiration included in the variations.

* * * * *